United States Patent [19]

Chatterjee

[11] Patent Number: 5,231,021

[45] Date of Patent: Jul. 27, 1993

[54] CLONING AND EXPRESSING RESTRICTION ENDONUCLEASES AND MODIFICATION METHYLASES FROM XANTHOMONAS

[75] Inventor: Deb K. Chatterjee, N. Potomac, Md.

[73] Assignee: Life Technologies, Inc., Gaithersburg, Md.

[21] Appl. No.: 866,362

[22] Filed: Apr. 10, 1992

[51] Int. Cl.$^5$ .................. C12N 9/10; C12N 9/22; C12N 15/54; C12N 15/55

[52] U.S. Cl. .................. 435/193; 435/199; 435/320.1; 435/252.34; 536/23.2

[58] Field of Search .................. 435/193, 199, 320.1, 435/352.34; 536/27, 23.2

[56] References Cited

U.S. PATENT DOCUMENTS 4,996,151 2/1991 Brooks et al. .................. 435/172.3
5,082,784 1/1992 Chatterjee et al. .................. 435/252.3

OTHER PUBLICATIONS

Chien et al., Cloning and Characterization of a Restriction and Modification System from *Neisseria gonorrhoeae* strain MS11, *Abstr. from the ASM Annual Meeting* p. 213 (1988).

Hammond et al., Cloning and Characterization of Restriction/Modification Enzymes From *Neisseria gonorrhoae*, Abstracts–1989 Meeting on Molecular Genetics of Bacteria and Phages, p. 91.

Hammond et al., Characterization of restriction enzyme from a strain of *Neisseria gonorrhoea* which recognizes 5'G ↓ CCGGC3', an isochizomer of *NaeI*, *Nucleic Acids Research* 17(8):3320 (1989).

Janulaitis et al., Cloning of the modification methylase gene of *Bacillus centrosporus* in *Escherichia coli*, *Gene* 20:197–204 (1982).

Kiss et al., Molecular cloning and expression in *Escherichia coli* of two modification methylase genes of *Bacillus subtilis*, *Gene* 21:111–119 (1983).

Kunkel et al., A Third Restriction Endonuclease from *Xanthomonas malvacearum*, J. Molec. Biol. 132:133–139 (1979).

Lunnen et al., Cloning type-II restriction and modification genes, *Gene* 74:25–32 (1988).

Mann et al., Cloning of Restriction and Modification Genes in *E. coli*: The HhaII System From *Haemophilus haemolyticus*, *Gene* 3:97–112 (1978).

Marmur, J., A procedure for the Isolation of Deoxyribonucleic Acid from Micro-organisms, *J. Mol. Biol.* 3:208–218 (1961).

Roberts, R. J., Restriction enzymes and their isoschizomers, *Nucleic Acids Research* 17(supp.):347–387 (1989).

Sullivan et al., Sequence analysis of the NgoPII methyltransferase gene from *Neisseria gonorrhoeae* P9: homologies with other enzymes recognizing the sequence 5'-GGCC-3', *Nuc. Ac. Res.* 16:4369–4387 (1988).

Sullivan et al., Characterization of DNA restriction and modification activities in *Neisseria* species, *FEMS Microbiology Letters* 44:389–393 (1987).

Szomolanyi et al., Cloning the modification methylase gene of *Bacillus sphaericus* R in *Escherichia coli*, *Gene* 10:219–225 (1980).

Walder et al., Cloning of the MspI Modification Enzyme, *J. Biological Chemistry* 258(2):1235–1241 (1983).

Wilson, G. G., Type II restriction-modification systems, TIG 4(11):314–318 (1988).

Wilson, G. G., Organization of restriction-modification systems, *Nucleic Acids Research* 19(10):2539–2566 (1991).

Wilson, G. G., Cloned restriction-modification systems—a review, *Gene* 74:281–289 (1988).

Yanulaitis et al., Specificity of New Restrictases and Methylases. Unusual Modification of Cytosine in Position 4, Plenum Pub. Corp. pp. 93–106 (1984)–translated from *Mol. Biol.* (Moscow) pp. 115–129 (1983).

*Primary Examiner*—Charles L. Patterson, Jr.
*Attorney, Agent, or Firm*—Sterne, Kessler, Goldstein & Fox

[57] ABSTRACT

The present invention is directed to recombinant hosts which contain and express XhoI and XhoII Type II restriction endonuclease and/or M.XhoI and M.XhoII modification methylase genes. The present invention is also directed to vectors or DNA molecules which contain these genes, and to methods of producing these enzymes. One source of these enzymes is *Xanthomonas campestris* pv. holcicola, although other microorganisms may be used to isolate the restriction endonuclease isoschizomers and modification methylase isoschizomers of this invention.

17 Claims, 1 Drawing Sheet

CLONING AND EXPRESSING RESTRICTION ENDONUCLEASES AND MODIFICATION METHYLASES FROM XANTHOMONAS

FIELD OF THE INVENTION

The invention is directed to recombinant DNA molecules encoding restriction endonuclease and modification methylase genes from the genus Xanthomonas, specifically *Xanthomonas campestris* pv. holcicola (formerly classified as *Xanthomonas holcicola*) and to hosts transformed with, and capable of expressing said genes. Specifically, the invention is directed to recombinant hosts and vectors which contain genes coding for the restriction endonucleases XhoI and XhoII and their corresponding methylases M.XhoI and M.XhoII.

The invention is further directed to cloned restriction endonuclease and modification methylase isoschizomers of these enzymes.

BACKGROUND OF THE INVENTION

Restriction endonucleases are a class of enzymes which occur naturally in prokaryotic and eukaryotic organisms. When they are purified away from other contaminating cellular components, restriction endonucleases are used in the laboratory to cleave DNA molecules into precise fragments. Thus, restriction endonucleases have proved to be indispensable tools in modern genetic research.

Restriction endonucleases cleave DNA by first recognizing and binding to particular sequences of nucleotides (the "recognition sequence") along the DNA molecule. The enzyme cleaves both strands of the DNA molecule within, or to one side of, this recognition sequence. The cleavage site can be blunt ended, both of the DNA strands are cleaved at the same nucleotide, or cleaved asymmetrically to yield a 3' or 5' overhang. Restriction endonucleases isolated from different sources most often have an affinity for different recognition sequences. About 100 kinds of different endonucleases have so far been isolated, many from microorganisms. Each restriction endonuclease is identified by its recognition sequence and by the cleavage pattern it exhibits when a target DNA, i.e. pBR 322, is digested by the particular enzyme.

A number of restriction endonucleases, called restriction endonuclease isoschizomers, have been isolated from unrelated microorganisms. Isoschizomers are enzymes which recognize the same recognition sequence. In some cases, though recognizing the same recognition sequence, the isoschizomers may cleave at different phosphodiester bonds within or to one side of the recognition sequence.

Modification methylases, complementary to their corresponding restriction endonucleases, recognize and bind to the same recognition sequence. Modification methylases chemically modify certain nucleotides within the recognition sequence by the addition of a methyl group, rendering the sequence resistant to cleavage by the complementary restriction endonuclease. Thus, in nature, methylases serve a protective function, i.e., to protect the DNA of an organism which produces the complementary restriction enzyme.

Restriction enzymes and modification methylases can be purified from the host organism by growing large amounts of cells, lysing the cell walls, and purifying the specific enzyme away from the other host proteins by extensive column chromatography. However, the amount of restriction enzyme relative to that of the other host proteins is usually quite small. Thus, the purification of large quantities of restriction enzymes or methylases by this method is labor intensive, inefficient, and uneconomical. By cloning the genes encoding for the desired restriction and modification enzymes and over expressing them in a well studied organism, generally *Escherichia coli* (*E. coli*), the amount of these enzymes, relative to that of the host proteins, may be increased substantially.

SUMMARY OF THE INVENTION

The present invention is directed to genes encoding Type II restriction endonucleases and to genes encoding modification methylases. The restriction endonucleases and modification methylases of the present invention recognize the palindromic sequences:

5' C ↓ TCGA G 3'

3' G AGCT ↑ C 5'.

The isoschizomers of this class of endonucleases are exemplified by XhoI, and cleave the sequence between the first C and T residues from the 5' end, producing a four-base 5' overhang.

5' R ↓ GATC Y 3'

3' Y CTAG ↑ R 5'.

The isoschizomers of this class of endonucleases are exemplified by XhoII, and cleave the sequence between the first R and G residues from the 5' end, producing a four-base 5' overhang where R is either A or G and Y is either T or C.

The methylase enzymes of the present invention chemically modify these recognition sequences, rendering them resistant to cleavage by the complementary restriction enzyme.

Specifically, the present invention discloses the cloning of genes encoding the restriction endonucleases, XhoI and XhoII, and the modification methylase complementary to these endonucleases, M.XhoI and M.XhoII.

The present invention is further directed to vectors and expression vectors containing the genes of the present invention.

The present invention is further directed to recombinant hosts transformed with the genes, vectors, and expression vectors of the present invention.

The present invention is further directed to methods for obtaining large quantities of substantially pure XhoI, XhoII, M.XhoI and M.XhoII.

DEFINITIONS

Figure 1:
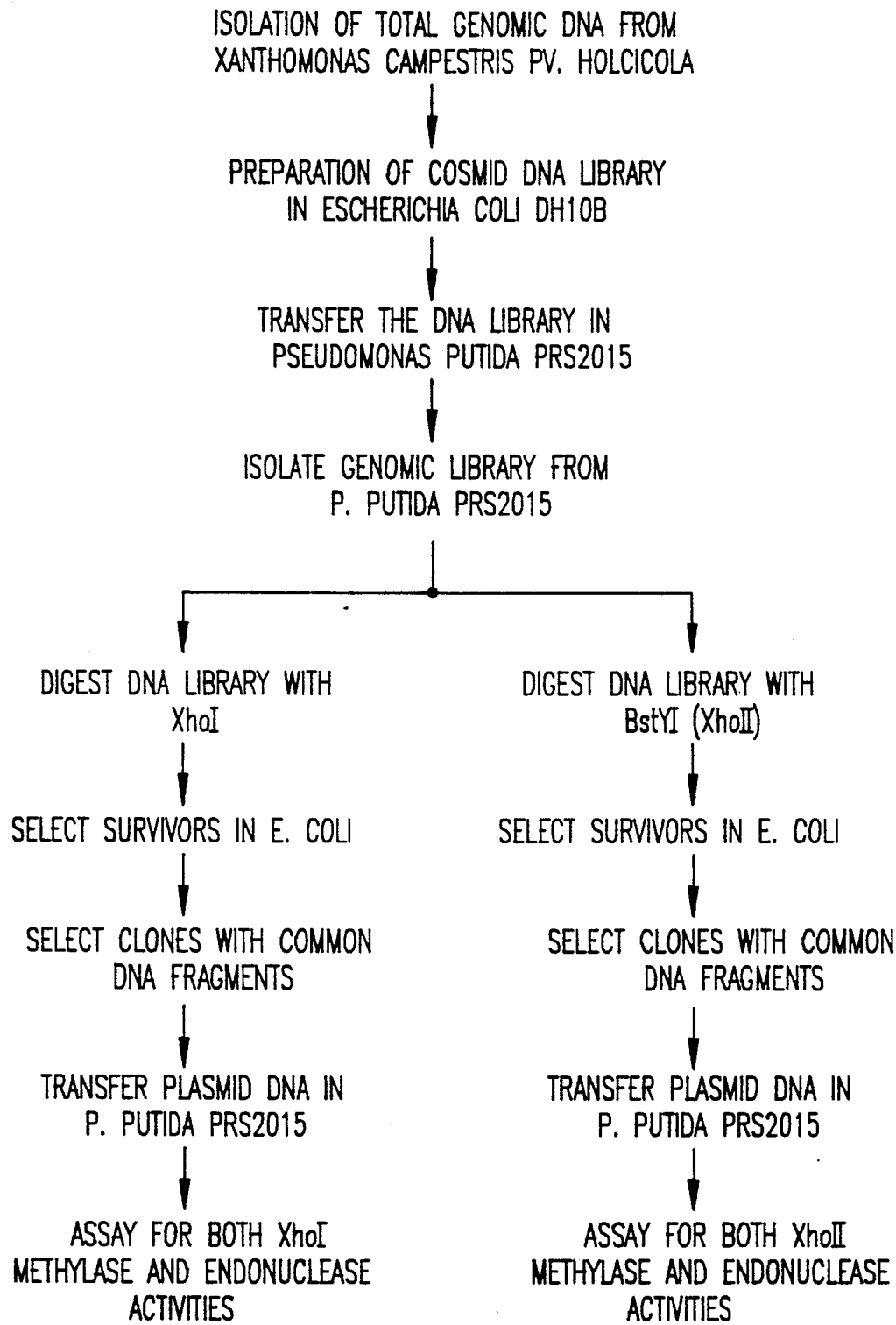
FIG. 1 shows the strategy employed to clone the restriction and methylase genes from *Xanthomonas campestris* pv. holcicola.

In the description that follows, a number of terms used in recombinant DNA (rDNA) technology are extensively utilized. In order to provide a clear and consistent understanding of the specification and claims, including the scope to be given such terms, the following definitions are provided.

CLONING VECTOR

A plasmid, a virus, or other DNA sequence which is capable of autonomously replicating within a host cell, or is capable of integrating into the chromosome of a host cell. Cloning vectors typically contain one or a small number of restriction endonuclease recognition sites into which DNA may be inserted. The cloning vector may further contain a marker suitable for use in the identification of cells transformed with the cloning vector, for example, resistance to an antibiotic such as ampicillin.

EXPRESSION VECTOR

A vector similar to a cloning vector but which contains DNA sequences which are capable of directing or enhancing the expression of an operably linked, gene. A cloned gene is usually placed under the control of (i.e., operably linked to) certain control sequences within the expression vector, such as a promoter sequence, using techniques well known in the art.

SUBSTANTIALLY PURE

As used herein, a restriction endonuclease is said to be "substantially pure" when the desired purified enzyme is essentially free of contaminating cellular components, such components being associated with the desired enzyme in nature. Contaminating cellular components may include, but are not limited to, phosphatases, exonucleases or other undesirable endonucleases.

RESTRICTION ENDONUCLEASE ISOSCHIZOMER

A restriction endonuclease isoschizomer is a term used to designate a group of restriction endonucleases which recognize and bind to the same recognition sequence but are isolated from different microbial sources. The isoschizomers may or may not cleave the same phosphodiester bonds within the recognition sequence.

MODIFICATION METHYLASE ISOSCHIZOMER

A modification methylase isoschizomer is a term used to designate a group of modification methylases which recognize the same recognition sequence but are isolated from different microbial sources. The isoschizomers may or may not chemically modify the same nucleotides within the recognition sequence.

RECOGNITION SEQUENCE

A recognition sequence is the DNA sequence which a particular restriction endonuclease and modification methylase recognizes and binds to. Recognition sequences are typically four to six (and in some cases eight) nucleotides in length and posses a two fold axis of symmetry (palindromic).

HOST

A prokaryotic or eukaryotic organism.

RECOMBINANT HOST

Any prokaryotic or eukaryotic microorganism which contains a desired cloned gene(s). This term is meant to include only those microorganisms which have been genetically altered to contain the desired gene(s). Organism which served as the source of the cloned gene(s) is not within the scope of this term unless that cell was altered to contain additional copies of the gene(s).

RECOMBINANT VECTOR

A cloning vector or expression vector which has been modified to contain a desired gene(s).

PROMOTER

A DNA sequence, generally located 5' (proximal) to the coding region of a gene, which is capable of directing the transcription of an operably linked gene(s) in a host.

GENE

A DNA sequence which contains an open reading frame capable of encoding an RNA sequence.

STRUCTURAL GENE

A DNA sequence which can be transcribed into messenger RNA and then translated into a sequence of amino acids.

EXPRESSION

Expression is the process by which a structural gene produces a polypeptide. It involves transcription of the gene into messenger RNA (mRNA) and translation of the transcribed mRNA into polypeptide(s).

Nomenclature for naming restriction endonucleases are in accord with the proposal of Smith et al., *J. Mo. Biol.* 81:419–423 (1973). Briefly, the first letter "X" of XhoI and XhoII designates the genes "Xanthomonas" while the lower case letters "ho" designate the species "holcicola."

DETAILED DESCRIPTION OF THE INVENTION

The present invention is directed to gene(s) encoding Type II restriction endonucleases which recognizes the palindromic sequence 5' CTCGAG 3', cleaving between the first C and T residues from the 5' end, producing a four-base 5' overhang, an example of this class of enzyme is XhoI. The present invention is further directed to gene(s) encoding Type II restriction endonucleases which recognized the palindromic sequence 5' RGATCY 3', cleaving between the first R and G residues from the 5' end, producing a four-base 5' overhang. An example of this enzyme is XhoII. The double-stranded recognition site of these enzymes are thus characterized as follows:

(XhoI)

(XhoII)

(wherein G represents deoxyguanosine, C represents deoxycytidine, A represents deoxyadenosine, T represents deoxythimadine, R represents deoxyadenosine or deoxyguanosine, and Y represents deoxycytidine or deoxythimadine).

The present invention is further directed to gene(s) encoding the modification methylase genes which are complementary to the XhoI and XhoII restriction endonuclease. These methylases chemically modify certain nucleotides within the recognition sequence by the addition of a methyl group, thus making the modified sequence resistant to cleavage by the complementary restriction endonuclease.

Also provided in the present invention are vectors, expression vectors, and recombinant hosts which contain the genes of the present invention (XhoI and XhoII and M.XhoI and M.XhoII).

I. Isolation of the Genes Encoding Restriction Endonucleases and Modification Methylases of the Present Invention or Isoschizomers thereof The restriction endonucleases and the corresponding modification methylases of the present invention may be obtained from any strain of *Xanthomonas campestris* pv. holcicola. Genes encoding isoschizomers of these enzymes can be obtained from any genus including, but not limited to, Arthrobacter, Bacillus, *(Bacillus stearothermophilus* Y produces the enzyme BstYI, an isoschizomer of XhoII), Citrobacter, Enterobacter, Escherichia, Flavobacterium, Haemophilus, Klebsiella, Micrococcus, Xanthomonas, Nocardia, Pseudomonas, Salmonella, and Streptomyces. The preferred genus to isolate isoschizomers of the modification methylases and restriction endonucleases of the present invention is Xanthomonas.

Any strain of Xanthomonas capable of producing restriction endonuclease isoschizomers of XhoI and XhoII—or modification methylase isoschizomers of M.XhoI and M.XhoII—can be used for the purpose of this invention. These include, but are not limited to, *Xanthomonas amaranthicola, Xanthomonas badrii, Xanthomonas campestris, Xanthomonas citrii, Xanthomonas cyanopsidis, Xanthomonas holcicola, Xanthomonas malvacearum, Xanthomonas manihotis, Xanthomonas nigromaculans, Xanthomonas oryzae, Xanthomonas papavericola*, and *Xanthomonas phaseoli*. Any species of Xanthomonas may also be used to isolate the genes coding for the modification methylase isoschizomers of M.XhoI and M.XhoII.

The preferred species for obtaining the genes encoding enzymes of the present invention is *Xanthomonas campestris* pv. holcicola as described in the examples.

II. Cloning and Expressing the Genes Encoding for the Restriction Endonucleases and Modification Methylases of the Present Invention or Isoschizomers thereof Genes encoding XhoI, XhoII, M.XhoI, M.XhoII, or isoschizomers thereof, can be inserted into a cloning vector and introduced into a host cell such that the cloned gene is expressed by the host cell in accordance with conventional techniques, including restriction digestion to provide appropriate termini, filling in of cohesive ends as appropriate, alkaline phosphatase treatment to avoid undesirable joining, and ligation with appropriate ligases (Sambrook et al., *Molecular Cloning*, Cold Spring Harbor Press, N.Y. (1989)).

a. Hosts for Cloning and Expressing

The present invention encompasses the expression of the desired restriction endonuclease or modification methylase in prokaryotic and eukaryotic cells. Eukaryotic and prokaryotic hosts that may be used for cloning and expressing the enzymes of the invention are well known in the art. Vectors which replicate in such host cells are also well known.

Preferred prokaryotic hosts include, but are not limited to, bacteria of the genus Escherichia, Bacillus, Streptomyces, Pseudomonas, Salmonella, Serratia, Xanthomonas, etc. The most preferred prokaryotic host is *P. putida* PRS2015.

b. Methods for Cloning and Expressing

Four different techniques for isolating and cloning restriction endonucleases and modification methylases have been described in a recent review by Wilson, "Cloned restriction-modification system—a review," *Gene* 74:281-289 (1988). The four methods reviewed include (1) subcloning of natural plasmids; (2) selection based on phage restriction; (3) selection based on vector modification involving methylation protection; and (4) multi-step isolation.

The preferred method according to the present invention is the vector modification technique, i.e., methylation protection. Methylation protection involves digestion of a plasmid library with the restriction enzyme to be cloned so that only plasmids whose sequences are modified, because of the presence of the methylase, will produce transformants in a suitable host. This selection has worked for cloning endonuclease and methylase genes together as well as methylase genes alone (Szomolanyi et al., 1980; Janulaitis et al., 1982; Walder et al., 1983; Kiss and Baldanf, (1983); Wilson, 1988, and Wilson, *Nucleic Acids Res.* 19:2539-2561 (1991).

The methylation protection method for cloning restriction endonuclease genes relies on the proximity of the methylase and restriction enzyme genes to each other and on the expression of both genes in the host cell such as *E. coli*. However, in the present invention, the preferred host is *P. putida*.

First, a library is constructed by ligating fragmented genomic DNA from the source organism into a vector. For this library, one chooses a vector having one or, preferably, more recognition sites of the restriction enzyme one wishes to clone. Preferably, vector pCP13 is used to construct the plasmid library (Darzins, A. et al., *J. Bacteriol.* 159:9-18 (1984)). Generally, partial digestion of the genomic DNA is used to prepare the library inserts.

Second, the library is transformed into and grown in a suitable host. In the present invention *E. coli* was initially the host and triparental mating was employed to transfer the library into *P. putida*. Vector DNA that is then isolated from the recombinant host cells is called the plasmid library.

The plasmid library isolated is a mixture of different DNA molecules and is representative of most if not all of the DNA sequences contained in the source organism. The vector/insert combinations containing the methylase gene will have methylated the recognition sequences within the vector/insert DNA.

The isolated plasmid library DNA is then digested with the restriction enzyme. Unmethylated vector/insert combinations are degraded whereas methylated combinations survive the endonuclease treatment. The endonuclease-treated DNA is then transformed into a fresh host cell. Digested plasmids do not transform the host. Non-digested plasmids, those that were methyl-protected, will transform and replicate themselves in the new host cells, thereby forming clones.

Cell extracts of these clones are then assayed for restriction endonuclease activity in order to identify clones which express the desired restriction enzyme or the plasmids of the transformed host are isolated and analyzed for the presence of a common restriction fragment. Thus, genes for a methylase-restriction system can be cloned on a single recombinant DNA molecule, provided that the restriction endonuclease gene is closely linked to the methylase gene.

There are a number of reasons why the above method might not work with a particular endonuclease-methylase system. (1) The two genes (methylase and endonuclease) may not be closely linked. In that case both genes cannot be on the same DNA fragment insert. (2) The cloned fragment may, by chance, contain only the methylase gene. For example, a closely linked endonuclease gene might be inactivated by being cut by the restriction enzyme that generated the DNA library. Similarly, the methylase and endonuclease genes may have been separated from each other by a cut at an intervening restriction site. (3) The level of expression of the endonuclease may be high relative to the expression level of the methylase. In this situation, before the expressed methylase can protect the host DNA, the expressed endonuclease destroys the vector/insert combination as well as degrade the chromosome(s) and may kill the host cell. Alternatively, deletion(s) resulting in loss of part or all of the endonuclease gene from the vector/insert combination may allow the host to survive. (4) The methylase gene may not be expressed in the new host, leading to lack of protection of DNA from the endonuclease. (5) The endonuclease gene may not be expressed in the new host. In situations (1) and (3), if the endonuclease is expressed in the host, there will be no methylase enzyme activity to protect DNA in the host cell and the attempt to clone the endonuclease would fail.

The present invention is based on the discovery that the genes encoding XhoI, and M.XhoI, and XhoII and M.XhoII respectively are closely linked and thus it is possible to clone the restriction enzyme gene using the methylation protection technique. However, it was found that these genes are not expressed in E. coli and therefore another less characterized host system was employed, that of Pseudomonas putida. Further, the expression of the XhoI and XhoII genes using the naturally occurring promoter to direct expression was virtually undetectable in E. coli. Thus, an additional selection was required to select clones containing the XhoI and XhoII restriction/modification system genes. This additional selection involved a comparison of vector DNA inserts to determine those clones which were related.

Although the steps outlined above are the preferred mode for practicing the present invention, it will be apparent to those skilled in the art that the above-described approach can vary in accordance with techniques known in the art. For example, once the XhoI and XhoII methylase and/or restriction genes are cloned based on the information disclosed herein, these gene sequences or synthetic oligonucleotides of these sequences may be used in hybridization experiments to obtain clones which contain these genes. Furthermore, one of ordinary skill in the art, using standard hybridization techniques, can utilize these sequences to isolate genes which encode for isoschizomers of the XhoI and XhoII restriction and modification enzymes by altering the hybridization stringencies.

c. Methods for Enhancing Expression

Once the desired restriction endonuclease and modification methylase genes have been isolated, a number of recombinant DNA strategies exist for enhanced production of the recombinantly produced proteins in eukaryotic or prokaryotic hosts. These strategies, which will be appreciated by those skilled in the art, utilize high copy number cloning vectors, expression vectors, inducible high copy number vectors, efficient promoters, etc.

Enhanced production of these enzymes can be accomplished, for example, by operably linking the desired gene(s) to a strong prokaryotic promoter, although the natural methylase or restriction gene promoter may be used. Such well known promoters may be either constitutive or inducible. Examples of constitutive promoters include the int promoter of bacteriophage λ, and the bla promoter of the β-lactamase gene of pBR322, etc. Examples of inducible prokaryotic promoters include the major left and right promoters of bacteriophage λ ($P_L$ and $P_R$), the trp, recA, lacZ, gal, trc, and tac promoters of E. coli, the α-amylase (Ulmanen, I., et al., J. Bacteriol. 162: 176–182 (1985)), the §-28-specific promoters of B. subtilis (Gilman, M. Z., et al., Gene 32: 11–20 (1984)), the promoters of the bacteriophages of Bacillus (Gryczan, T. J., In: The Molecular Biology of the Bacilli, Academic Press Inc., New York (1982), and Streptomyces promoters (Ward, J. M., et al., Mol. Gen. Genet. 203: 468–478 (1986)). Prokaryotic promoters are reviewed by Glick, B. R., (J. Ind. Microbiol. 1: 277–282 (1987)); Cenatiempo, Y. (Biochimie 68: 505–516 (1986)); and Gottesman, S. (Ann. Rev. Genet. 18: 415–442 (1984)).

In order to enhance the production of the desired restriction endonuclease in a prokaryotic cell, it is important to maintain expression of the corresponding modification methylase gene sufficient to protect the DNA of the recombinant host against cleavage with the cloned restriction endonuclease. Therefore, it may be necessary to enhance the level of methylase expression in conjunction with increased endonuclease activity.

Furthermore, those skilled in the art will recognize that both the restriction endonuclease and modification methylase genes need not be maintained on the same cloning or expression vector within the same recombinant host. The endonuclease gene, for example, may be located on one vector, while its corresponding methylase gene may be located on a separate vector or located on the host genome. Various combinations of maintaining both the modification and restriction genes within the same recombinant host can be constructed. The only requirement, when cloning restriction endonuclease genes, is that the recombinant host contain and express the methylase gene complementary to the endonuclease gene being cloned.

III. Isolation and Purification of the Restriction Endonucleases and Modification Methylase Enzymes from Recombinant Hosts The enzymes of this invention, XhoI, XhoII, M.XhoI, and M.XhoII, or isoschizomers thereof, are preferably produced by fermentation of a recombinant host containing and expressing the cloned restriction endonuclease and/or modification methylase genes. A recombinant host, such as E. coli or P. putida producing the cloned proteins, can be grown and harvested according to techniques well known in the art.

After culturing, the recombinant host cells of this invention can be separated from the culture liquid, for example, by centrifugation. The methylase and/or restriction enzymes produced by this host enzymes can be extracted and purified by using known protein purification techniques commonly employed for these types of enzymes.

In general, the collected microbial cells are dispersed in a suitable buffer, and then broken down by ultrasonic treatment to allow extraction of the enzyme by the buffer solution. After removal of the residue by ultracentrifugation, the desired enzyme can be purified by extraction, ion-exchange chromatography, molecular-sieve chromatography, affinity chromatography, and the like, giving the restriction endonuclease or modification methylase of this invention.

According to the present invention, assays to detect the presence of the restriction endonucleases and modification methylases can be used during the conventional biochemical purification methods to determine the presence of these enzymes.

Restriction endonuclease can be identified on the basis of the cleavage of its recognition sequence, for example, Adenovirus-2 (Ad-2) DNA or λ DNA may be used as a substrate. The DNA fragments obtained are separated electrophoretically using agarose gel electrophoresis.

Demonstration of modification methylase activity can be, but is not limited to, a two-step identification process. First, substrate DNA (for example, Ad-2 DNA) containing the recognition sequence is incubated with the fractions to be tested for methylase activity. Secondly, this DNA is then challenged with the complementary restriction endonuclease to identify those fractions which contain methylase activity. For example, while assaying for M.XhoI, the DNA samples will be challenged with XhoI. Assaying for M.XhoII, the DNA samples can be challenged with either XhoII or BstYI, an isoschizomer of XhoII. Thus, DNA samples which are not cleaved by XhoI contain M.XhoI activity and samples which are not cleaved by XhoII or BstYI contain M.XhoII activity.

The recombinant host *Pseudomonas putida* PRS2015 containing the genes coding for XhoI and M.XhoI, designated (XhoI-1), and the recombinant host *Pseudomonas putida* PRS2015 containing the genes coding for XhoII and M.XhoII, designated (XhoII-1), were put on deposit on Apr. 7, 1992 with the Patent Culture Collection, Northern Regional Research Center, USDA, 1815 N. University Street, Peoria, Ill. 61604 USA (NRRL) as deposit nos. NRRL B-18956 and B-18957, respectively.

Having now generally described the invention, the same will be more readily understood through reference to the following Examples which are provided by way of illustration, and are not intended to be limiting of the present invention, unless specified.

EXAMPLE 1

Bacterial Strains and Growth Conditions

*E. coli* strains were grown at 37° C. or 30° C. in Circle Grow (Bio101), Luria Broth (LB: yeast extract 0.5%, tryptone 1%, NaCl 0.5%) or LB-maltose (LB+0.2% Maltose). *Pseudomonas putida* was grown either in LB or Pseudomonas Isolation Agar (PIA) (Difco) at 30° C. Antibiotic concentration were as follows: for *E. coli*: ampicillin, 100 µg/ml; tetracycline, 20 µg/ml; kanamycin, 50 µg/ml; and for *Pseudomonas putida*: tetracycline, 50 µg/ml in LB or 300 µg/ml in PIA. *E. coli* DH10B was obtained from Life Technologies, Inc. (LTI). *Pseudomonas putida* PRS2015 was originally obtained from Prof. Nick Ornston (Yale University, New Haven). *Xanthomonas campestris* pv. holciola ATCC 13461 (a producer of XhoI, XhoII, M.XhoI and M.XhoII) was obtained from the American Type Culture Collection, Rockville, Md.

EXAMPLE 2

DNA Isolation

Small scale plasmid DNA isolation was performed by the alkaline lysis method (Maniatis et al. (1982) *Molecular Cloning: A laboratory manual*, Cold Spring Harbor Laboratory). For large scale preparation, the alkaline lysis procedure was followed by CsCl-gradient centrifugation (Maniatis et al., supra).

*X. campestris* pv. holciola total genomic DNA was prepared according to Murmur (1961) J. Mol. Biol. 3:208–218.

EXAMPLE 3

Construction of Genomic Library

Genomic DNA of *X. campestris* pv. holcicola was digested partially with PstI as follows: 100 µg of purified DNA was taken in 1000 µl 1X React 2 (LTI) buffer. The DNA was aliquoted into 9 tubes 100 μl each except the first tube contained 200 μl. 10 units (1 μl) of PstI was added to the first tube and mixed well. A 100 μl aliquot was serially transferred to the next tube and so on. Therefore tube 1–8 tubes contained 10 μg DNA and each tube contained one-tenth less PstI than the previous tube. Each sample was incubated at 37° C. for 1 hour and 5 μl of the sample from each tube was applied in 0.9% agarose gel to visualize the extent of digestion. Tubes 4 and 5 were chosen because these two tubes displayed minimal digestion. The DNA was ethanol precipitated and dissolved in 10 μl TE (TE=10 mM Tris.HCl, pH 8.0, 1 mM EDTA).

3 μg of PstI cleaved and dephosphorylated pCP13 was ligated with 0.5 μg of each partial DNAs (tubes 4 and 5) separately in a 30 μl 1X Ligase buffer (LTI) in the presence of 1 unit of T4 DNA ligase for 16 hours at room temperature.

5 μl of the ligated DNAs were packaged in λ Packaging Extract (LTI) using the protocol recommended by the manufacturer. After the packaging was complete, *E. coli* cells were infected with the packaging mix as follows: DH10B cells were prepared by growing an overnight culture in LB containing 0.2% maltose plus 10 mM $MgSO_4$. The next day, 25 ml of fresh same media was inoculated with 500 μl of an overnight culture and grown to mid-log phase ($A_{590}$=0.681). These cells were then centrifuged and resuspended in 2 ml of sterile 10 mM $MgSO_4$. 100 μl of the cell suspension was mixed with 200 μl of packaging mix. After 15 minute incubation at 37° C. without sharing a 700 μl of SOC (2% tryptone, 0.5% yeast extract, 10 mM NaCl, 2.5 mM KCl, 10 mM $MgCl_2$, 10 mM $MgSO_4$ and 20 mM glucose) was added and incubated at 37° C. for 1 hour. The cells were then plated onto LB-agarose plates containing kanamycin and incubated overnight.

Approximately $8\times10^3$ kanamycin resistant clones were pooled by scraping the cells from the agar plates. This was accomplished by flooding each plate with 5 ml of LB. A portion of the pooled clones (5 ml) was inoculated immediately into 500 ml LB containing kanamycin and grown at 30° C. After 5 hours of growth, the cells were harvested. Plasmid DNA was isolated according to Example 2. The cell library was called the Xho Library and the plasmid library was designated pCPXhoL.

EXAMPLE 4

Selection of clones expressing methylase and restriction enzymes in *E. coli*

Clones expressing XhoI methylase and XhoII methylase were selected by digesting pCPXhoL with XhoI and BstYI (an XhoII isoschizomer) respectively. To select M.XhoI and M.XhoII, each 2 µg of pCPXhoL was digested separately with 50 units of XhoI or 30 units of BstYI. After 2 hours of digestion, the digested DNAs were dephosphorylated with calf intestine phosphatase (LTI) by the recommended protocol. The DNAs were extracted with phenol:chloroform (1:1), ethanol precipitated and dissolved in 50 µl TE (10 mM Tris.HCl, pH 8.0, 1 mM EDTA) for XhoI-digested DNA and 10 µl TE for BstYI-digested DNA. 5 µl BstYI-digested DNA was redigested with 30 units of BstYI as above, dephosphorylated, ethanol precipitated and finally dissolved in 6 µl TE.

*E. coli* DH10B electro-competent (LTI) cells were with electroporated with 200 ng of XhoI-digested DNA. *E. coli* DH10B competent cells were also transformed with 200 ng of XhoI-digested DNA. The protocols were as described in the LTI product profile. A total of 184 colonies were obtained from both electroporation and transformation.

Twelve clones that survived XhoI digestion were individually inoculated and grown overnight in 2 ml Circle-Grow containing kanamycin. The DNA preparations were then retested for their ability to resist cleavage with XhoI by standard protocol. 0.5–1.0 µg of DNA was digested in 1X React 2 (LTI) buffer with 10 units of XhoI for 1 hour in a 20 µl reaction. Protection of the plasmid and the chromosomal DNA from the digestion would indicate the presence of M.XhoI activity. None of the 12 clones demonstrated any protection against XhoI suggesting that none of these clones contain any M.XhoI activity. In addition, none of these clones produced common fragments upon digestion with PstI, the enzyme used for generating the DNA library.

For selection of M.XhoII, *E. coli* DH10B competent cells were transformed with approximately 500 ng of BstYI-digested DNA by the recommended protocol (LTI). Only 6 colonies were obtained in LB-agar plates containing kanamycin. All 6 clones were grown separately as above and the plasmid and the chromosomal DNA were retested for their resistance to BstYI digestion. Again, none of these 6 clones displayed any M.XhoII activity as both resident plasmid and chromosomal DNA were digested with BstYI.

From the above, it was concluded that both M.XhoI and M.XhoII are not expressed in *E. coli*. The promoter sequences of M.XhoI or M.XhoII may not be recognized by the *E. coli* RNA polymerase or the translation of the mRNA encoding the methylase genes may not be enough to provide protection. In order to overcome these potential problems, attempts were made to select both M.XhoI and M.XhoII, as well as their corresponding endonucleases, in Pseudomonas.

EXAMPLE 5

Introducing Xho Library in Pseudomonas

Since M.XhoI or M.XhoII methylase could not be selected in *E. coli*, an alternative expression system was used. In order to select the methylase gene(s) in Pseudomonas, first, the Xho DNA Library made in *E. coli* (Example 3) was introduced into *Pseudomonas putida* PRS2015. pCP13 is a broad host range plasmid and can be transferred into a variety of gram negative bacteria using triparental conjugation (Ditta et al., *Proc. Natl. Acad. Sci. USA* 77:7347–7351 (1980)).

The Xho Library (Example 3) in *E. coli* DH10B was grown overnight in LB containing tetracycline. *Pseudomonas putida* PRS2015 was grown in LB and *E. coli* HB101, containing helper plasmid pRK2013 (Ditta, supra) was grown in LB and kanamycin. After overnight growth 1 ml culture of DH10B/Xho Library and HB101/pRK2013 were centrifuged to remove the antibiotic-containing medium. The cells were suspended in 1 ml fresh LB. Aliquots of 0.25 ml each of *P. putida* PRS2015, DH10B/Xho library, and HB101/pRK2013 were mixed and filtered through a 0.45 µm Millipore filter. The filter was incubated at 30° C. on LB agar plate for 5 hours. The cells were suspended in 1 ml LB and 0.1 ml samples were plated (10 plates) on PIA containing tetracycline. The plates were incubated overnight at 30° C.

More than 10,000 colonies were obtained per plate. Colonies from 3 plates were scraped and pooled as described in Example 4. A 5 ml aliquot was inoculated in 1 liter LB containing tetracycline and grown for 5 hours at 30° C. The cells were harvested and plasmid DNA was isolated from PRS2015 as described in Example 2.

EXAMPLE 6

Selecting clones containing M.XhoI and M.XhoII in Pseudomonas

For selection of XhoI and XhoII methylases, the DNA library obtained from PRS2015 was treated with XhoI and BstYI respectively. 5 µg DNA was used for each selection. Digestion with XhoI and BstYI were done according to the recommended protocol, however the digestion was continued for 5 hours. 50 units of XhoI and 30 units of BstYI were used for the selection. The DNAs, following digestion, were treated as described in Example 4.

Since, transformation of Pseudomonas with the plasmid DNA is not as efficient as in *E. coli*, the digested DNA(s) were transformed into *E. coli* and the *E. coli* transformants were examined for plasmid DNA with common bands upon digestion with PstI. *E. coli* DH10B competent cells were transformed as described in Example 4 and transformants were selected on LB-agar plates containing tetracycline. XhoI selection yielded a total of 47 clones and BstYI selection yielded a total of 240 clones. Four clones from each selection plates were inoculated for small scale plasmid preparation.

Plasmid DNAs from *E. coli* were tested for common fragments. For XhoI-selected clones, 2 clones (called XhoI-1 and XhoI-2) out of 4 clones showed two common PstI fragments (~10 kbp and 7 kbp). When the plasmids were tested with XhoI for their resistance, they showed partial protection. For BstYI selected clones, 3 out of 4 clones showed more than 6 common PstI fragments and 2 of them (XhoII-1 and XhoII-4) were identical. Plasmid DNA from these clones were, however, completely sensitive to BstYI.

Plasmid DNA from 2 XhoI-selected clones (XhoI-1 and XhoI-2) (showing common bands) and 2 BstYI (XhoII-1, XhoII-4)-selected clones were individually introduced into *Pseudomonas putida* PRS2015 by triparental conjugation. PRS2015/XhoI-1 and PRS2015/XhoI-2 and pRS2015/XhoII-1 and PRS2015/XhoII-4 were selected. The plasmid and chromosomal DNA isolated from PRS2015/XhoI-1 and PRS2015/XhoI-2 were completely protected against digestion with XhoI. Similarly, plasmid and chromosomal DNA from PRS2015/XhoII-1 and PRS2015/XhoII-4 were completely protected against BstYI. These results suggest that both M.XhoI and M.XhoII are expressed very efficiently in *Pseudomonas putida*.

EXAMPLE 7

Expressing XhoI and XhoII restriction enzyme in *E. coli*

To determine XhoI and XhoII activities in an *E. coli* background, *E. coli* DH10B cells containing XhoI-1 and XhoI-2 as well as DH10B containing XhoII-1 and XhoII-4 were grown in 20 ml LB containing tetracycline at 30° C. and the cell extracts were assayed for XhoI and XhoII activities, respectively. None of the DH10B/XhoI-1 or DH10B/XhoI-2 showed any detectable XhoI activity. Similarly, no XhoII activity could be detected in DH10B containing either XhoII-1 or XhoII-4.

EXAMPLE 8

Expressing XhoI and XhoII restriction endonuclease activity in *Pseudomonas putida*

PRS2015/XhoI-1 or XhoI-2 displayed XhoI methylase activity in *P. putida*. However, only partial methylase activity and no restriction enzyme activity could be detected in *E. coli*. To determine whether the clones contain the gene for XhoI restriction enzyme, PRS2015 containing both XhoI-1 and XhoI-2 were grown in LB with tetracycline and the cell extracts were assayed for XhoI enzyme activity. Both clones displayed XhoI activity estimated at approximately 100,000 units per gram of cells.

For XhoII activity, PRS2015 containing XhoII-1 and XhoII-4 were grown as above and the extracts were assayed for XhoII activity. Both clones displayed XhoII activity estimated at approximately 10,000 units per gram of cells.

The results above suggested that XhoI, XhoII, M.XhoI and M.XhoII are not expressed in *E. coli*, but are expressed, however, in Pseudomonas.

EXAMPLE 9

Assay for restriction enzymes in the crude cell extracts 20 ml cultures in LB plus antibiotic were centrifuged, and the cell pellets were resuspended in 0.9 ml of cold SB (10 mM Tris.HCl, pH 8.0, 10 mM β-mercaptoethanol, 1 mM EDTA). The cells were transferred to a 1.5 ml microcentrifuge tube and sonicated three times with 10 seconds bursts at a 100% duty cycle using a microtip probe. The cellular debris was removed by centrifugation for 5 min at 14,000 xg at 4° C. Adenovirus-2 (Ad-2) or phage lambda DNA (λ DNA) was prepared in 1 X REact 2 ® buffer (LTI)(50 mM Tris HCl, pH 8.1, 10 mM MgCl$_2$, 50 mM NaCl) for XhoI or in 1 X REact 8 ® buffer (LTI)(20 mM Tris HCl, pH 7.4, 10 mM MgCl$_2$) for XhoII, respectively, such that 20 µl contained 1 µg of DNA. 20 µl aliquots of the substrate were dispensed in several tubes except the first tube contained 25 µl sample. 5 µl of the cell extract was added to the first tube, then 10 µl of the contents were transferred serially through 4 or more tubes. The reactions were incubated for 60 minutes at 37° C. and analyzed on an agarose gel. Activity was determined by the presence of the appropriate size bands associated with XhoI-digested Ad-2 DNA or BstYI-digested (for XhoII) λ DNA. BstYI digestion was carried out at 60° C. as recommended by the manufacturer.

What is claimed is:

1. A gene encoding an XhoI restriction endonuclease or an M.XhoI modification methylase, which recognizes the palindromic sequence:

5′C ↓ TCGAG3′

3′GAGCT ↑ C5′ wherein said endonuclease cleaves said sequence between the first C and T residues from the 5′ end, producing a four-base 5′ overhang.

2. The gene of claim 1, wherein said gene is obtained from *Xanthomonas campestris* pv. holcicola.

3. The gene of claim 2, wherein said Xanthomonas is *Xanthomonas campestris* pv. holcicola ATCC 13461.

4. The gene of claim 1, wherein said gene codes for XhoI.

5. The gene of claim 1, wherein said gene codes for M.XhoI.

6. A *Pseudomonas putida* host transformed with any of the genes of any one of claims 1 to 5.

7. A vector containing any of the genes of any one of claims 1 to 5.

8. The vector at claim 7, wherein said vector is an expression vector.

9. The vector of claim 7, wherein said vector contains two genes, a first gene encoding a restriction endonuclease and a second gene encoding the complementary methylase.

10. The vector of claim 9, wherein said gene(s) is under control of an inducible promoter.

11. The vector of claim 10, wherein said promoter is a lambda P$_L$ promoter.

12. The vector of claim 10, wherein said promoter is a tac promoter.

13. A method of producing an XhoI restriction endonuclease or an M.XhoI modification methylase which recognizes the palindromic sequence:

5′C ↓ TCGAG3′

3′GAGCT ↑ C5′ wherein said endonuclease cleaves said sequence between the first C and T residues from the 5′ end, producing a four-base 5′ overhang, said method comprising the steps of:

(a) culturing a recombinant *P. putida* host capable of expressing any of the genes of any one of claims 1–5; and (b) isolating said restriction endonuclease or said modification methylase from said host.

14. The method of claim 13, wherein said gene is obtained from *Xanthomonas campestris* pv. holcicola.

15. The method of claim 14, wherein said gene is obtained from *Xanthomonas campestris* pv. holcicola ATCC 13461.

16. The method of claim 13, wherein said gene encodes XhoI.

17. The method of claim 13, wherein said gene encodes M.XhoI.

* * * * *